United States Patent
Iyer

(12) 
(10) Patent No.: US 6,837,899 B1
(45) Date of Patent: Jan. 4, 2005

(54) DUAL PURPOSE BALLOON CATHETER

(76) Inventor: Sriram Iyer, 201 E. 87th St., Apt. 14C, New York, NY (US) 10128

( * ) Notice: Subject to any disclaimer, the term of this patent is extended or adjusted under 35 U.S.C. 154(b) by 171 days.

(21) Appl. No.: 10/288,213

(22) Filed: Nov. 6, 2002

(51) Int. Cl.⁷ ............................................. A61M 29/00
(52) U.S. Cl. ..................................................... 606/200
(58) Field of Search ................................ 606/200, 113, 606/127, 114, 106, 159; 623/1.11

(56) References Cited

U.S. PATENT DOCUMENTS 6,179,859 B1 * 1/2001 Bates et al. ................. 606/200
6,540,722 B1 * 4/2003 Boyle et al. ................. 606/200

* cited by examiner

*Primary Examiner*—Kevin T. Truong
(74) *Attorney, Agent, or Firm*—Kajane McManus

(57) ABSTRACT

The dual purpose balloon catheter provides for not only dilation of a structure such as a stent or section of vasculature but also provides for removal of a filter from a point downstream of the distal end of the catheter in a single procedure.

7 Claims, 1 Drawing Sheet

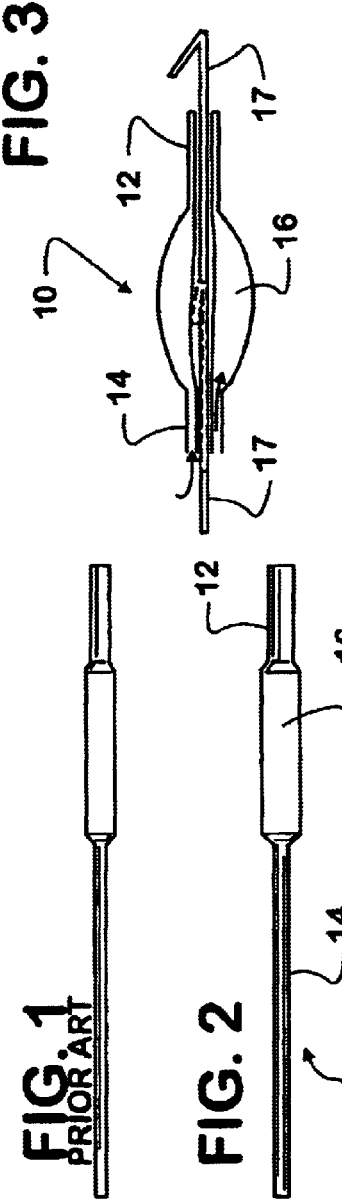
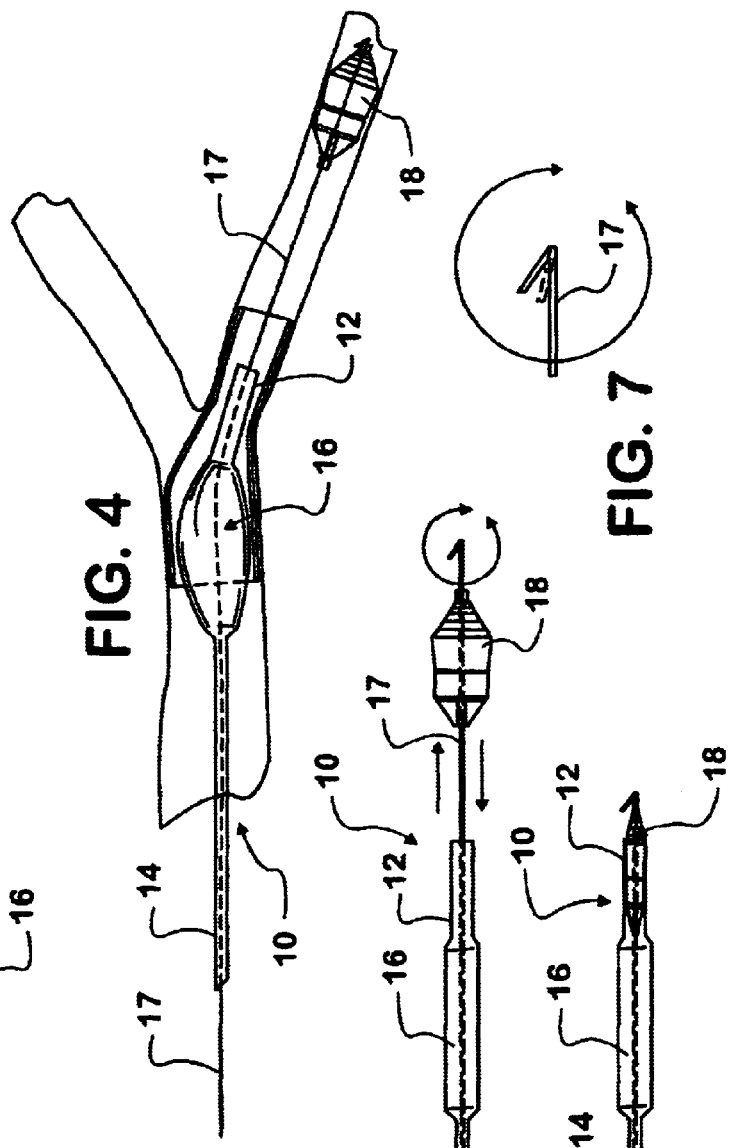
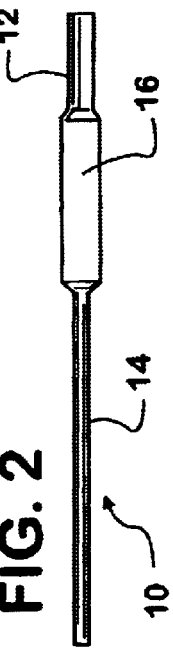
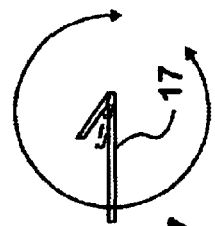

DUAL PURPOSE BALLOON CATHETER

BACKGROUND OF THE INVENTION

1. Field of the Invention

The present invention provides a dual purpose balloon catheter. In particular, the catheter is used not only for purposes of expansion of a tubular structure, such as a stent, but is also used to capture and remove a filter typically positioned downstream or cephalad to the catheter prior to insertion of the balloon catheter.

2. Prior Art

Heretofore, a balloon catheter has been used solely for expansion of a tubular biological structure, e.g., a section of a vessel or a prosthesis, e.g., a stent, or section of vasculature. A filter, typically positioned downstream or cephalad to the balloon catheter, prior to introduction thereof, which assists in trapping material ("embolic debris") loosened during the expansion of the balloon as in the case of compression of plaque in an angioplasty procedure, has typically been removed in a secondary procedure after withdrawal of the balloon catheter, adding more time for completion of the procedure, and requiring further invasion and trauma to the body structures, and in particular, the walls of the vasculature.

Accordingly, there is a need to combine procedures, which the catheter of the present invention accomplishes.

SUMMARY OF THE INVENTION

According to the invention there is provided a dual purpose balloon catheter comprising a proximal sleeve, a distal sleeve, and a balloon interposed between the sleeves. The central lumen of the proximal sleeve, balloon and distal sleeve are contiguous such that a wire can pass through the proximal sleeve, balloon lumen and distal sleeve and exit out through the tip of the distal sleeve. If a wire is already in place inside the vasculature, the lumen of the distal sleeve can be used to thread the wire. The wire extends into and through the proximal sleeve, the balloon and the distal sleeve, and is further extendable to engage at a distal end thereof an expandable filter which is retractable by the wire into the distal sleeve, the filter collapsing as it enters the distal sleeve, with the catheter and filter being removed simultaneously without need of a second procedure to remove the filter.

BRIEF DESCRIPTION OF THE DRAWINGS

FIG. 1 is a perspective view of a prior art balloon catheter.

FIG. 2 is a perspective view of the dual purpose balloon catheter made in accordance with the teachings of the present invention.

FIG. 3 is a cross sectional view through a distal end of the catheter of FIG. 2.

FIG. 4 shows the catheter of FIG. 2 within vasculature being used to engage a filter downstream or cephalad thereof.

FIG. 5 is similar to FIG. 3, without the vasculature being shown.

FIG. 6 shows the filter being drawn into a distal sleeve of the balloon catheter.

FIG. 7 is an enlarged view of the distal end of the wire of the catheter used to engage the filter for simultaneous removal thereof with the catheter.

DESCRIPTION OF THE PREFERRED EMBODIMENTS

Balloon catheters, as iterated above, are known in the art. Typically the distal sleeve of such prior art balloon catheter has accommodated a wire, as has a proximal sleeve of such catheter, with an expandable balloon of the catheter being interposed between the distal and proximal sleeves.

Various embodiments of filters, which are typically positioned downstream of, or cephalad to, an area of vasculature being manipulated by either simple dilation or through positioning of a stent or the like therein, for trapping any matter being loosened by the manipulation are also known. Such self expanding filters are typically positioned in the vasculature prior to introduction of the catheter.

Prior art catheters cannot be used to remove such filter and a secondary invasive procedure is necessary for removal of the filter.

The distal sleeve of prior art catheters cannot accommodate ensnarement of such filter therein; thus the need for a the secondary procedure for ensnarement and removal of the filter.

Turning now the FIGS. 2–7, there is illustrated therein the dual purpose balloon catheter made in accordance with the teachings of the present invention and generally identified by the reference numeral 10.

As shown, the catheter 10 includes a distal sleeve 12, a proximal sleeve 14 and an expandable balloon portion 16 interposed between the distal and proximal sleeves 12 and 14, respectively.

In the preferred embodiment presented herein, it is preferred to form the distal sleeve 12 to accommodate a wire 17 or, in this case, filter 18 approximately up to 0.035 inch and to form the proximal sleeve 14 to accommodate a wire 17 of approximately up to 0.016 inch, which: is the same wire 17 shown exiting the distal sleeve 12 in FIGS. 3–5.

In use, the catheter 10 is fed into a vascular channel after a filter 18 has been appropriately positioned cephalad thereof.

Once dilation of the stent 34, or vasculature, as required, by the balloon 16 is accomplished in a desired manner, the balloon 16 is deflated, and the wire 17 is forced distally out of the distal sleeve 12 until engagement of a filter 18, previously inserted into the vasculature, is accomplished. Engagement of the filter 18 by the wire 17 is accomplished through provision of an arm or finger 36 pivotally engaged to the distal end 38 of the wire, as best illustrated in FIG. 7. The wire 17 extended through the filter 18 and the finger 36 pivots slightly outwardly from along the wire 17 as it engages against the material of the filter 18 as the distal end 38 of the wire 17 is pulled proximally back into the material of the filter 18. The filter 18 is then pulled, via the wire 17, into the distal sleeve 12 of the catheter 10, as best illustrated in FIG. 6. Next, the catheter 10 is removed, in known manner.

Thus, the catheter 10 of the present invention accomplishes not only dilation of the desired structure but removal of the distal filter 18 in a single procedure, eliminating the need for the typical secondary procedure presently required to remove the filter 18.

As described above, the dual purpose balloon catheter 10 and its method of use provide a number of advantages, some of which have been described above and others of which are inherent in the invention. Also, modifications may be proposed including equivalent structures and steps without departing from the teachings herein.

Accordingly, the scope of the invention is only to be limited as necessitated by the accompanying claims.

What is claimed is:

1. A dual purpose balloon catheter comprising a proximal sleeve, a distal sleeve, and an expandable balloon portion interposed between the sleeves, a wire extending into and through the proximal sleeve, the balloon and the distal sleeve, the wire, having a distal end configured such that it, when passed through an expandable filter cephalad of the catheter, engages the filter and retracts the filter into the distal sleeve, the filter collapsing as it enters the distal sleeve.

2. The catheter of claim 1 wherein the proximal sleeve can accommodate a wire of approximately up to at least 0.016 inch.

3. The catheter of claim 1 wherein the distal sleeve can accommodate a filter of approximately up to at least 0.035 inch.

4. The catheter of claim 1 wherein the distal end of the wire incorporates a pivotal finger.

5. The catheter of claim 4 wherein the pivotal finger pivots when engaged against material of the filter as the wire is pulled proximally back toward the distal sleeve.

6. The catheter of claim 4 wherein the pivotal finger pivots only slightly outwardly away from the wire.

7. The catheter of claim 4 where in the pivotal finger rests against and along the distal end of the wire as the wire is moved distally toward and through the material of the filter.

\* \* \* \* \*